United States Patent

Tonami et al.

[11] Patent Number: 5,965,893
[45] Date of Patent: Oct. 12, 1999

[54] X-RAY CT SOLID-STATE DETECTOR

[75] Inventors: Hiromichi Tonami; Jun-ichi Ooi; Mikio Wada; Ryoichi Sawada, all of Kyoto, Japan

[73] Assignee: Shimadzu Corporation, Kyoto, Japan

[21] Appl. No.: 08/882,337

[22] Filed: Jun. 25, 1997

[30] Foreign Application Priority Data

Jun. 28, 1996 [JP] Japan ................................. 8-169166

[51] Int. Cl.⁶ ........................................................ G01T 1/20
[52] U.S. Cl. ............................................... 250/370.11
[58] Field of Search ..................................... 250/370.11

[56] References Cited

U.S. PATENT DOCUMENTS 4,429,227  1/1984  DiBianca et al. ................... 250/367

FOREIGN PATENT DOCUMENTS

| 63-65392 | 3/1988 | Japan | 250/370.11 |
| 1-113691 | 5/1989 | Japan | 250/370.11 |
| 2-208591 | 8/1990 | Japan | 250/370.11 |

*Primary Examiner*—Constantine Hannaher
*Attorney, Agent, or Firm*—Armstrong, Westerman, Hattori, McLeland & Naughton

[57] ABSTRACT

An x-ray CT solid-state detector provided with detector blocks each having a substrate, a photodiode array secured to the substrate and a scintillator array secured to the photodiode array, and with a collimator device having a plurality of collimator plates secured to a support body, and arranged such that transmitted x-rays obtained by irradiating a fan-shape x-ray beam from an x-ray source onto a subject to be tested, are guided to the detector blocks through the collimator device. There is secured, to each substrate, a groove plate having at a predetermined position a groove into which a collimator plate is to be fitted. The scintillator and photodiode arrays are secured to each substrate with a predetermined positional relationship between the scintillator and photodiode arrays and the groove plate maintained. Each detector block and the collimator device are fixed to each other with a collimator plate fitted in the groove of the groove plate. The collimator plates are positioned directly with respect to the groove plates and the scintillator and photodiode arrays are fixed to the substrates with a predetermined positional relationship between the scintillator and photodiode arrays and the groove plates maintained. This enhances the precision with which the scintillator elements are positioned with respect to the collimator plates.

6 Claims, 7 Drawing Sheets

X-RAY CT SOLID-STATE DETECTOR

BACKGROUND OF THE INVENTION

1. Field of the Invention

The present invention relates to an x-ray CT solid-state detector, and more particularly to an x-ray CT solid-state detector arranged such that fan-shape x-rays transmitted through a subject to be tested are detected, through a collimator device, by a number of radiation detector elements disposed in the form of an array.

2. Description of the Related Art

Figure 15:
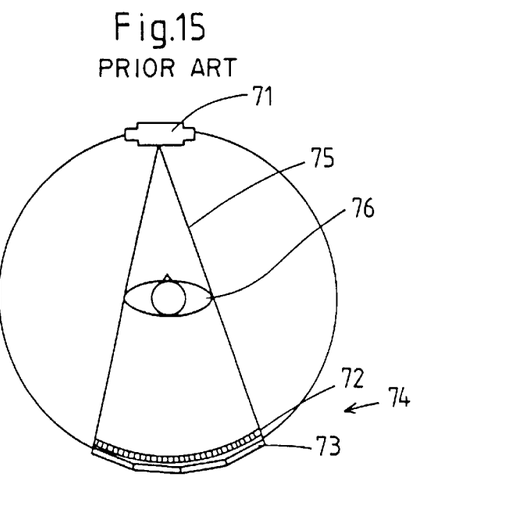
FIG. 15 is a view illustrating the arrangement of a general x-ray CT apparatus.

As generally shown in FIG. 15, a prior art x-ray CT apparatus comprises an x-ray CT solid-state detector comprising an x-ray tube 71, a collimator device 72 and detector blocks 73, and is arranged such that transmitted x-rays obtained by irradiating a fan-shape x-ray beam 75 from the x-ray tube 71 onto a subject to be tested, are guided to and detected by the detector blocks 73 through the collimator device 72.

In each of the detector blocks 73, combinations of scintillators for converting radiations into lights and photoelectric conversion elements for converting the lights into electric signals, are disposed in parallel on a substrate in the form of a one-dimensional array. In each block 73, 8 to 30 combinations of scintillators and photoelectric conversion elements are generally disposed on the substrate. Such detector blocks 73 are consecutively disposed in the form of a polygon on a predetermined circle and combined with the collimator device 72, thus forming the x-ray CT solid-state detector 74.

Figures 16A, 16B:
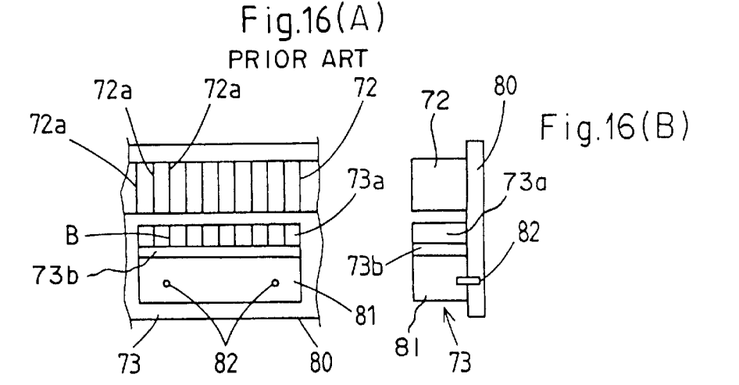
FIGS. 16(A) and 16(B) are views illustrating the arrangement of a solid-state detector of prior art used in an x-ray CT apparatus.

In such an x-ray CT solid-state detector, the collimator device 72 and each detector block 73 are secured to an attachment plate 80, as shown in FIG. 16. The collimator device 72 comprises a number of collimator plates 72a incorporated in a case-like support body (not shown in FIG. 16). Each of the collimator plates 72a is fixed to the attachment plate 80 through the support body such that each collimator plate 72a is directed to the point for generating x-rays. In each of the detector blocks 73, an assembly of a scintillator array 73a and a photodiode array 73b is fixed to a support stand 81. Each of the detector blocks 73 is fixed to the attachment plate 80 such that each detector block 73 and the collimator device 72 are made in a unitary structure. Each of the collimator plates 72a is required to be positioned A on each boundary B between adjacent scintillator elements. Accordingly, positioning pins 82 are disposed at the attachment plate 80. By fitting the pins 82 in fitting holes formed in the support stand 81 of the detector block 73, the collimator device 72 and each detector block 73 are positioned with respect to each other.

In such a prior art solid-state detector, the relative positional relationship between the collimator device 72 and the detector blocks 73 is determined only by the positioning pins 82. This disadvantageously makes it difficult to improve the positional precision. More specifically, the collimator plates 72a are held by the support body, and the scintillator arrays 73a are held by the support stands 81, and the support body and the support stands 81 are coupled through the attachment plates 80 and the pins 82. Thus, a number of members are interposed between the collimator plates 72a and the scintillator arrays 73a. This disadvantageously makes it difficult to improve the most important positional precision between the collimator plates 72a and the scintillator arrays 73a.

SUMMARY OF THE INVENTION

It is an object of the present invention to provide an x-ray CT solid-state detector having a relatively simple and economical arrangement capable of positioning, at all times, the collimator plates and the detector blocks with high precision.

To achieve the object above-mentioned, the present invention provides an x-ray CT solid-state detector which is provided with detector blocks each having a substrate, a photodiode array secured to the substrate and a scintillator array secured to the photodiode array, and with a collimator device having a plurality of collimator plates secured to a support body, and which is arranged such that transmitted x-rays obtained by irradiating a fan-shape x-ray beam from an x-ray source onto a subject to be tested, are guided to the detector blocks through the collimator device. There is secured, to each substrate, a groove plate having at a predetermined position a groove into which a collimator plate is fitted. The scintillator and photodiode arrays are secured to each substrate with a predetermined positional relationship between the scintillator and photodiode arrays and the groove plate maintained. Each detector block and the collimator device are fixed to each other with a collimator plate fitted in the groove of the groove plate.

Each lateral wall of each groove has such a thickness as not to interfere with the collimator plates adjacent to the collimator plate fitted into the groove.

According to the x-ray CT solid-state detector having the arrangement above-mentioned, the scintillator and photodiode arrays of each detector block are secured to the substrate with a predetermined positional relationship with respect to the groove plate maintained.

Further, with a collimator plate fitted in the groove of the groove plate, each detector block and the collimator device are fixed in a unitary structure. According to the arrangement above-mentioned, the collimator plates are positioned directly with respect to the groove plates, and the scintillator and photodiode arrays are secured to the substrates with predetermined positional relationships with respect to the groove plates maintained. Accordingly, the precision with which the scintillator elements and the collimator plates are positioned with respect to each other, can be improved as compared with the arrangement of prior art in which the scintillator elements are positioned, using the pins disposed at the designed positions, through various members such as support diodes, attachment plates and the like.

According to a preferred embodiment of the present invention, each of the groove plates is a rectangular plate having a width equal to that of each substrate and is provided on a face thereof with a projecting portion extending in the widthwise direction thereof, and the projecting portion is provided at the center thereof with a convex port on provided in the top thereof with a groove which extends along the center line dividing the width of the groove plate into two equal parts and which has such width and depth that a collimator plate is fitted in the groove.

Alternatively, each groove plate may be a groove plate which has a groove, which is made substantially in the form of L in section, which is disposed, adjacent to the scintillator and photodiode arrays, on that surface of each substrate on which the arrays are mounted. Also, each groove plate may be a rod-like groove plate which has a groove and which is disposed adjacent to the scintillator and photodiode arrays.

According to the present invention, the x-ray CT solid-state detector may be arranged such that each substrate is provided in a predetermined position thereof with a groove into which a collimator plate is fitted, that there are secured, to each substrate, scintillator and photodiode arrays with the center axes thereof aligned with the center axis of the groove, that a collimator plate to be fitted into the groove has such a shape as to stride over the scintillator and photodiode arrays, and that the collimator plate is fitted into the groove.

According to the arrangement above-mentioned, too, the collimator plates are positioned directly with respect to the groove plates and there are secured, to the substrates, the scintillator and photodiode arrays with predetermined positional relationships thereof with respect to the groove plates maintained. This improves the positioning precision with which the scintillator elements are positioned with respect to the collimator plates.

According to the arrangement above-mentioned, there may be used each substrate having, at predetermined positions thereof, a pair of blocks attached thereto, each block having a groove into which the collimator plate is to be fitted. According to this arrangement, the grooves are not formed directly in the substrates but are formed in the blocks attached to the substrates. This increases the degree of freedom in designing as to the material to be selected of the blocks, the heights of the grooves from the substrates and the like, causing the blocks to be made in an optimum shape.

BRIEF DESCRIPTION OF THE DRAWINGS

FIG. 8 (A) is a perspective view of a usual collimator plate used in the collimator device 2 in FIG. 6;

FIG. 8 (B) is a perspective view of a collimator plate which is used in the collimator device 2 in FIG. 6 and which has fitting portions to be fitted in a groove formed in a substrate;

DETAILED DESCRIPTION OF PREFERRED EMBODIMENTS

The following description will discuss preferred embodiments of the present invention with reference to drawings.

Figure 1:
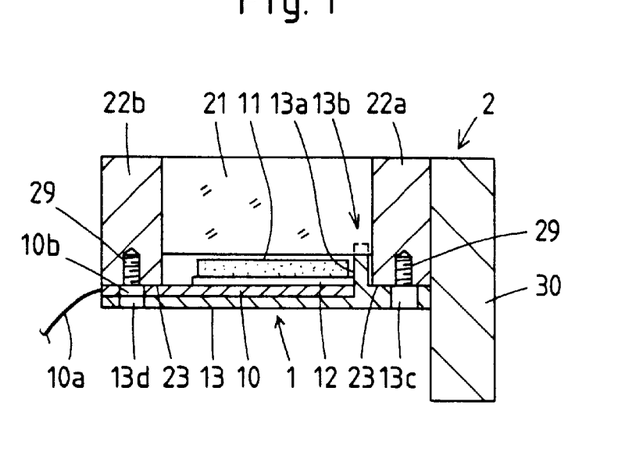
FIG. 1 vertical section view illustrating the arrangement of an embodiment of the present invention.
Figure 2:
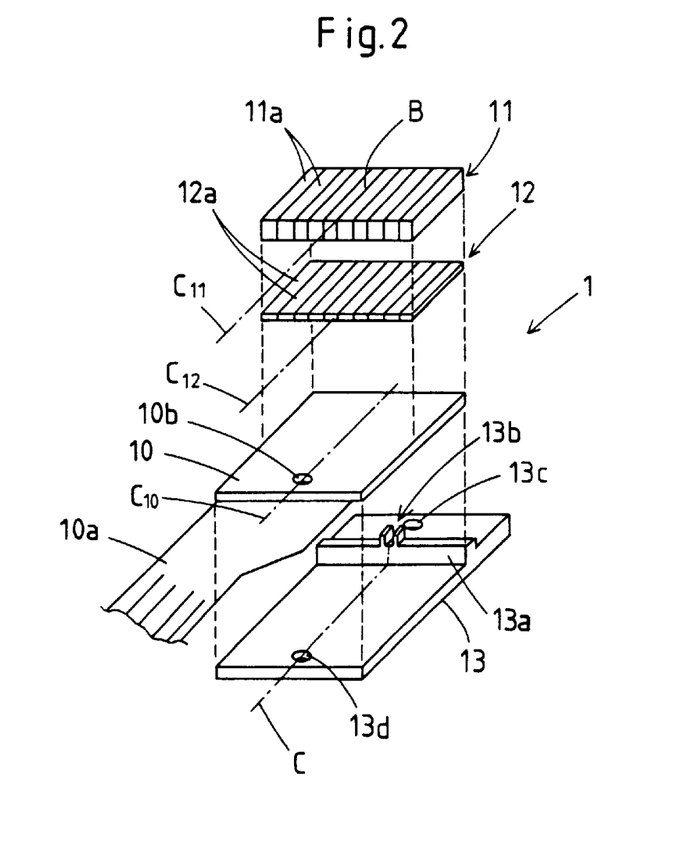
FIG. 2 is a exploded perspective view of a detector block 1 in FIG. 1.
Figure 3:
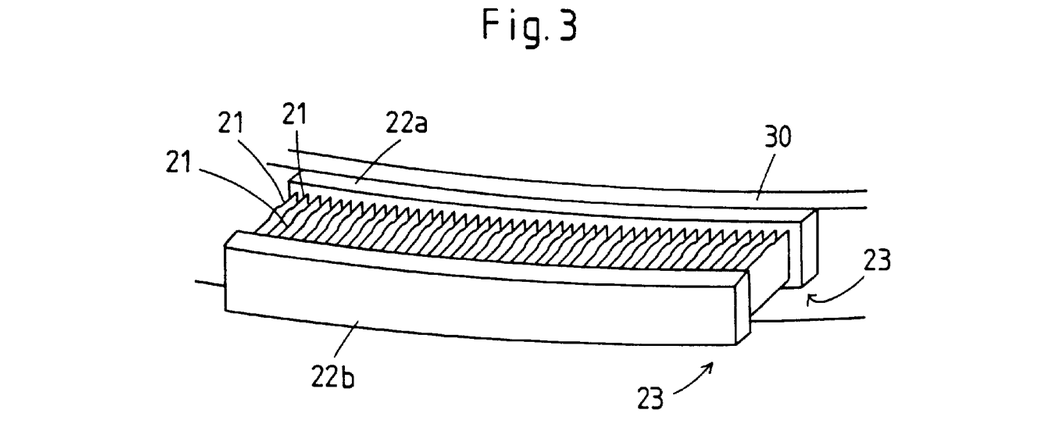
FIG. 3 is a perspective view of main portions of the collimator device 2 in FIG. 1.

FIG. 1 is a vertical section view illustrating the arrangement of an embodiment of the present invention, FIG. 2 is an exploded perspective view of a detector block 1 in FIG. 1, and FIG. 3 is a perspective view of main portions of the collimator device 2.

As shown in FIG. 2, each detector block 1 comprises (i) a substrate 10 to which attached is a signal line cable 10a connected to photodiodes 12a to be discussed later, (ii) a scintillator array 11 on which a plurality of scintillator elements 11a are disposed in the form of a one-dimensional array, and (iii) a photodiode array 12 on which the photodiodes 12a in number equal to that of the scintillator elements 11a are disposed also in the form of a one-dimensional array, the photodiode and scintillator arrays 12 and 11 being mounted on the substrate 10. In this embodiment, these arrays 11, 12 are fixed to the substrate 10 on the basis of a groove plate 13 secured to the underside of the substrate 10. The substrate 10 is provided in one end side thereof with a through-hole 10b with the use of which the substrate 10 is fixed to the collimator device 2 through the groove plate 13.

The groove plate 13 is made of a rectangular plate having a width equal to that of the substrate 10 and is provided on a face thereof with a projecting portion 13a extending in the widthwise direction of the plate. The projecting portion 13a is provided at the center thereof with a convex portion, and a groove 13b is formed in the top of the convex portion. The groove 13b is formed on the center line C which divides the width of the groove plate 13 into two equal parts. The groove 13b has such width and depth that a collimator plate 21 of the collimator device 2 is fitted therein. More specifically, the groove has a width of about 100 to about 300 µm and a depth of about 1 to about 1.5 mm. Each lateral wall of the groove 13b is so set as not to interfere with the collimator plates adjacent to the collimator plate fitted in the groove 13b. For example, the groove 13b is formed using a wire cut electric spark machine, a dicing saw or the like. The groove plate 13 is provided in both ends thereof with through-holes 13c, 13d with the use of which the groove plate 13 is fixed to the collimator device 2.

In this embodiment, the scintillator array 11 and the photodiode array 12 are fixed, according to the following procedure, to the substrate 10 with a predetermined positional relationship with respect to the groove 13b maintained.

More specifically, the photodiode array 12 is secured to the substrate 10 using adhesives or the like with the center axis C12 of the photodiode array 12 aligned with the center axis C10 of the substrate 10, and the scintillator array 11 is secured to the photodiode array 12 using adhesives or the like with the center axis C11 of the scintillator array 11 aligned with the center axis C12 of the photodiode array 12. More specifically, when each of the scintillator array 11 and the photodiode array 12 has even-numbered elements and the width of the substrate 10 is equal to the width of each of the scintillator array 11 and the photodiode array 12, the substrate 10, the scintillator array 11 and the photodiode array 12 can mutually be bonded with one lateral sides of the substrate 10, the scintillator array 11 and the photodiode array 12 located on the same plane. On the other hand, using adhesives or the like, the substrate 10 and the groove plate 13 can mutually be bonded to each other with one lateral sides of the substrate 10 and the groove plate 13 located on the same plane and with one longitudinal end of the substrate 10 coming in contact with one lateral face of the projecting portion 13a. By such assembling, the scintillator array 11 and the photodiode array 12 are fixed to each other with a predetermined positional relationship with respect to the groove plate 13 maintained; that is, with the center line of each of the arrays 11, 12 aligned with the center line C of the groove plate 13. In such assembling, each of the arrays 11, 12 has even-numbered elements and the groove 13b is formed in the groove plate 13 on the center line C thereof. Accordingly, the element boundary B at the center of each of the arrays 11, 12 is located in the center of the groove 13b of the groove plate 13.

As shown in FIG. 3, the collimator device 2 comprises a number of collimator plates 21 secured at both ends thereof by supports 22a, 22b, and the support 22a is fixed at its lateral side to a main case body 30. The collimator device 2 is placed in an x-ray CT apparatus with each of the collimator plates 21 directed to a point-like x-ray source. Each of the collimator plates 21 is made of a thin plate which is high in x-ray shielding ability and of which atomic number is high such as tungsten, molybdenum or the like. The collimator plates 21 are equal in arrangement pitch with the elements of each of the scintillator array 11 and the photodiode array 12. As shown in the following, the collimator device 2 and the detector block 1 are fixed to each other such that each collimator plate 21 is located on each element boundary B of each of the arrays 11, 12.

More specifically, to enable the detector blocks 1 to be attached to the collimator device 2, each of the undersides of the supports 22a, 22b of the collimator device 2 is formed of a set of a plurality of flat contact faces 23 which are disposed, as conventionally done, at the zones into which the circumference of a circle is being divided, the polygon formed of these contact faces 23 being approximated to the circle. Each pair of contact faces 23 has internal threads 29 corresponding to the through-hole 10b of the substrate 10 and the through-holes 13c, 13d of the groove plate 13. Each detector block 1 is secured to each of the pairs of the contact faces 23.

Each detector block 1 is fixed to the collimator device 2 as set forth below. As shown in FIG. 1, a predetermined collimator plate 21 of the collimator device 2 is fitted in the groove 13b of the groove plate 13 of a detector block 1 such that the detector block 1 and the collimator device 2 are positioned in the element arrangement direction, and one end surface of the groove plate 13 is so disposed as to come in contact with a lateral side of the main case body 30 such that the detector block 1 and the collimator device 2 are positioned in the direction at a right angle to the element arrangement direction above-mentioned. Then, bolts (not shown) are inserted in the through-hole 10b of the substrate 10 and in the through-holes 13c, 13d of the groove plate 13, and then threaded into the internal threads 29, such that the detector block 1 is fixed to the collimator device 2. In such a fixed state, the groove 13b is located at the element boundary B at the center of each of the scintillator array 11 and the photodiode array 12. Accordingly, each collimator plate 21 is accurately located on each scintillator element boundary B of the detector block 1.

Each detector block 1 and the collimator device 2 are fitted to each other only at one position where a collimator plate 21 is fitted into the groove 13b of the detector block 1. However, each detector block 1 is positioned as coming in contact with the contact faces 23 of the supports 22a, 22b and with the surface of the main case body 30. Accordingly, when fastening the bolts after the detector block 1 and the collimator device 2 have been positioned, the detector block 1 is never moved due to friction even though the bolts are threaded in the internal threads 29 after positioned. To improve the positioning precision, that surface of the main case body 30 which comes in contact with each groove plate 13, is preferably improved in plane precision.

Figure 4:
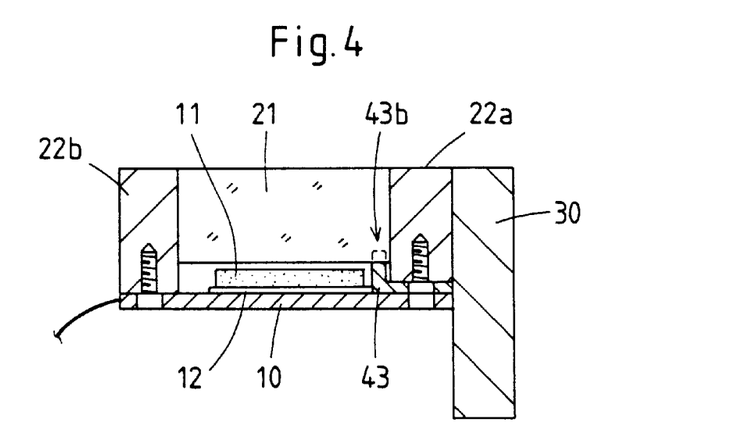
FIG. 4 is a vertical section view illustrating the arrangement of another embodiment of the present invention.

FIG. 4 is a vertical section view illustrating the arrangement of another embodiment of the present invention. In this embodiment in FIG. 4, a groove plate 43 substantially in the form of L in section having a groove 43b equivalent to the groove 13b in FIG. 2, is fixed to that surface of each substrate 10 on which a scintillator array 11 and a photodiode array 12 are mounted, the groove plate 43 being disposed adjacent to the arrays 11, 12. In this embodiment in FIG. 4, when each detector block 1 and the collimator device 2 are fixed to each other, a collimator plate 21 is fitted in the groove 43b of the groove plate 43, and the groove plate 43 is held by and between the substrate 10 and one support 22a of the collimator device 2.

Figure 5:
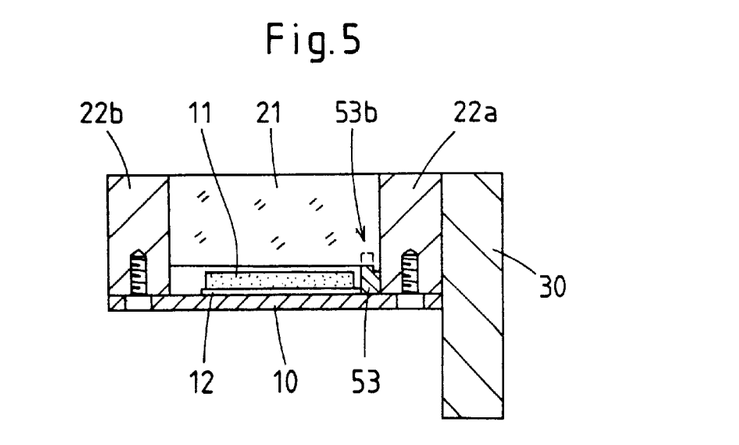
FIG. 5 is a vertical section view illustrating the arrangement of a further embodiment of the present invention.

FIG. 5 is a vertical section view illustrating the arrangement of a further embodiment of the present invention. In this embodiment in FIG. 5, a rod-like groove plate 53 having a groove 53b equivalent to the groove 13b in FIG. 2, is fixed to that surface of each substrate 10 on which a scintillator array 11 and a photodiode array 12 are mounted, the groove plate 43 being disposed adjacent to the arrays 11, 12. In this embodiment in FIG. 5, when each detector block 1 and the collimator device 2 are fixed to each other, a collimator plate 21 is fitted in the groove 53b of the groove plate 53, and the groove plate 53 comes in contact with a lateral surface of one support 22a of the collimator device 2.

Figure 6:
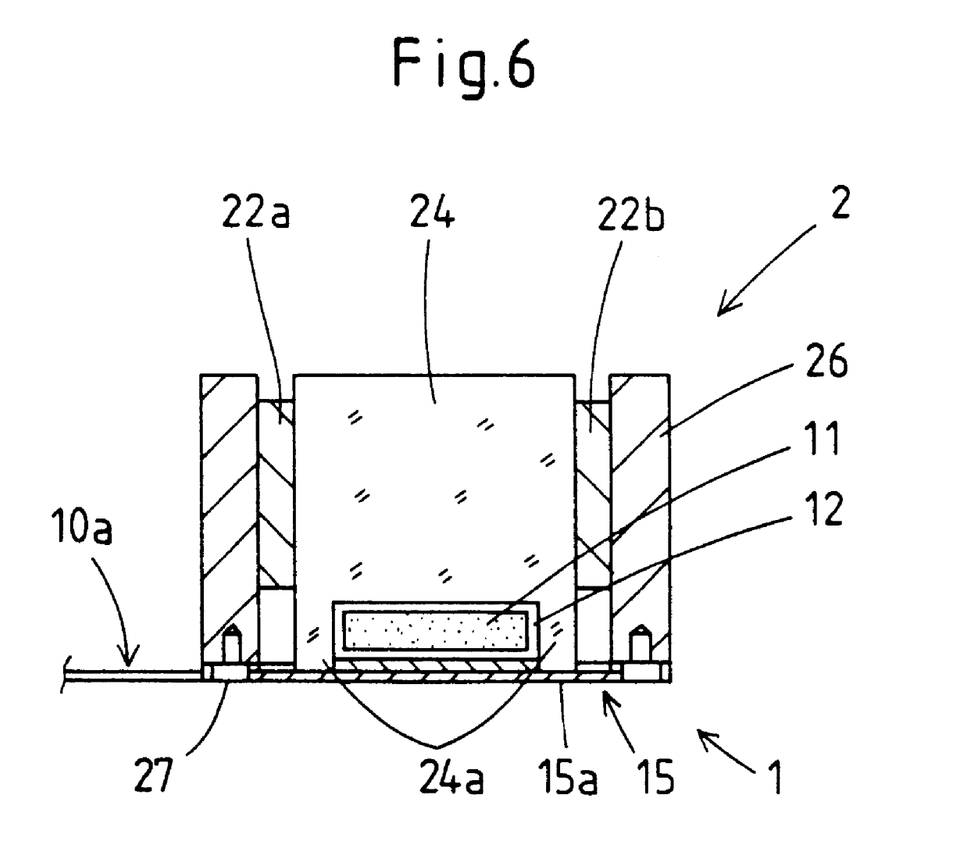
FIG. 6 is a vertical section view illustrating the arrangement of still another embodiment of the present invention.
Figure 7:
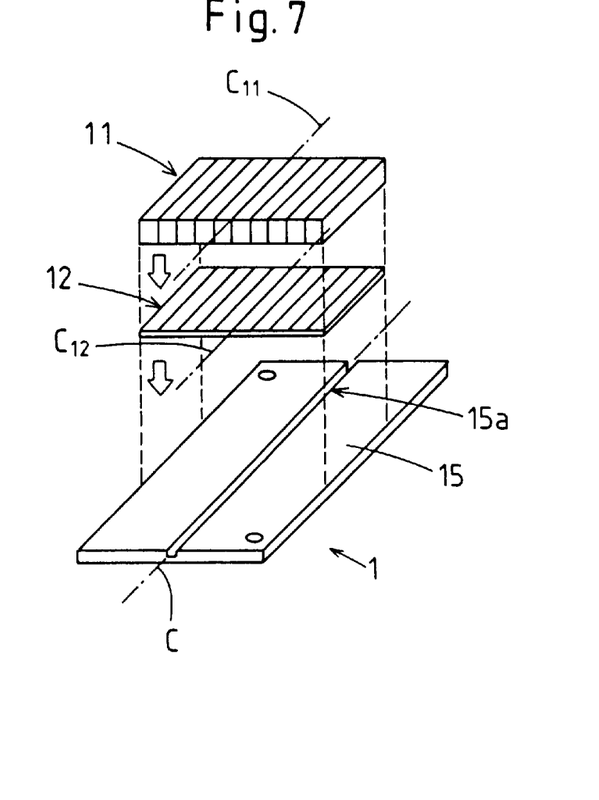
FIG. 7 is an exploded perspective view of a detector block 1n FIG. 6.
Figure 8A:
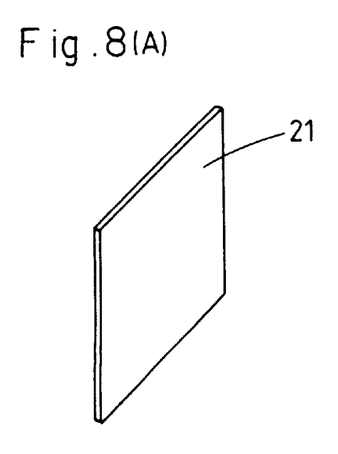
Figure 8B:
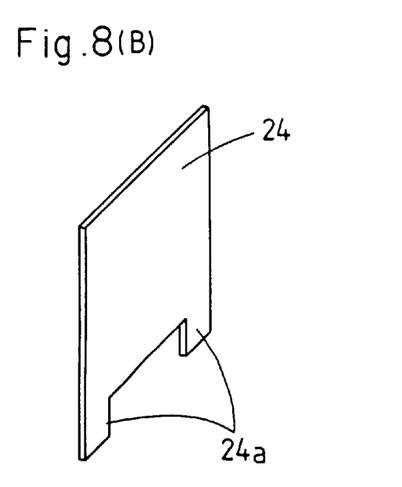
Figure 9:
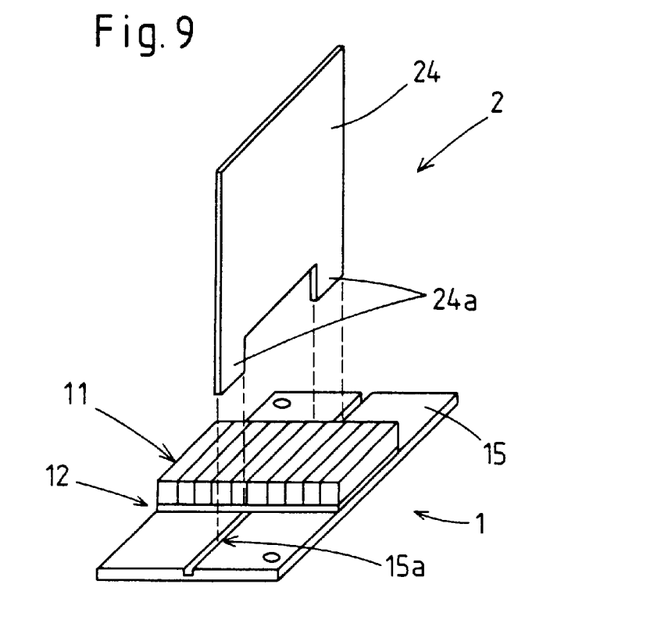
FIG. 9 is an exploded perspective view of a detector block 1 and the collimator device 2 in FIG. 6.

FIG. 6 is a vertical section view illustrating the arrangement of still another embodiment of the present invention. FIG. 7 is an exploded perspective view of a detector block 1 in FIG. 6. Each of FIG. 8(A) and FIG. 8(B) is a perspective view of a collimator plate used in the collimator device 2 in FIG. 6. FIG. 9 is an exploded perspective view of a detector block 1 and the collimator device 2 in FIG. 6.

A substrate 15 has a groove 15a on the center line C which divides the width of the substrate 15 into two equal parts. A photodiode array 12 is bonded to the substrate 15 with the center axis C12 of the photodiode array 12 aligned with the center line C of the substrate 10, and a scintillator array 11 is bonded to the ohotodiode array 12 with the center axis C11 of the scintillator array 11 aligned with the center axis C12 of the photodiode array 12. A collimator device 2 comprises a plurality of collimator plates 21 as shown in FIG. 3. However, this embodiment in FIG. 6 is different from each of the embodiments above-mentioned in that the collimator plates comprise two types of collimator plates, i.e., a usual collimator plate 21 as shown in FIG. 8(A) and a collimator plate 24 having fitting portions 24a as shown in FIG. 8(B). This embodiment in FIG. 6 is the same as each of the embodiments mentioned earlier in the distance between adjacent collimator plates and the number of the collimator plates. For example, when each detector block 1 has N scintillator elements, a collimator plate 24 having fitting portions 24a is inserted per N collimator plates and so disposed as to be located at the center of each collimator device block which corresponds to each detector block 1. More specifically, each detector block is disposed for each pair of contact faces 23 of the collimator device 2. The collimator plate at the center of each collimator device block is formed by a collimator plate 24 having fitting portions 24a, and other collimator plates are formed of usual collimator plates 21. By fitting the fitting portions 24a of the collimator plate 24 in the groove 15a of each substrate 15, each detector block 1 and the collimator device 2 are positioned with respect to each other. Thus, the relative positional relationship between the collimator device 2 and each detector block 1 is determined by fitting the fitting portions 24a of the collimator plate 24 in the groove 15a of the detector block 1 in its center, and the detector block 1 is fixed to the collimator device 2 with screws using case body fastening holes 27 formed in the substrate 15. Thus, usual collimator plates 21 are disposed adjacent each collimator plate 24 having fitting portions 24a and positioned at element boundary positions of the scintillator array.

Figure 10:
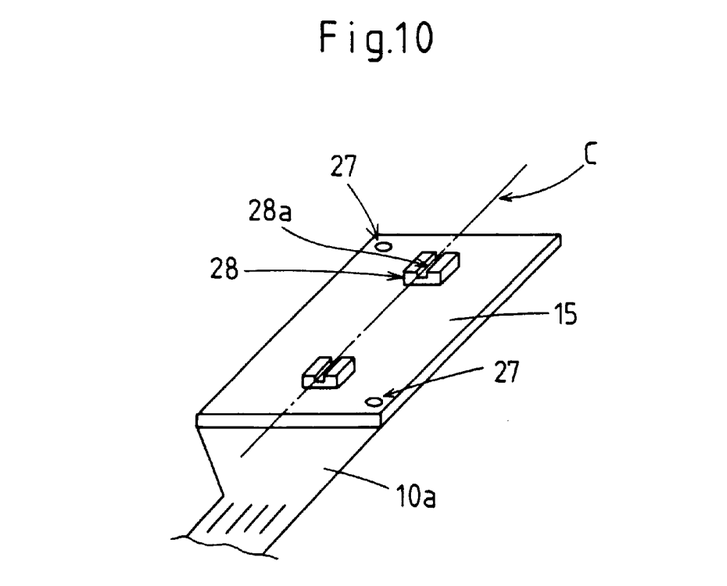
FIG. 10 is a perspective view illustrating the substrate 15 of detector block 1 of a still further embodiment of the present invention.

FIG. 10 is a perspective view of a substrate 15 of each detector block 1 in a still further embodiment of the present invention. In this embodiment in FIG. 10, each substrate 15 is not directly provided with a groove, but has blocks 28 attached thereto. Each block 28 has a groove 28a. Thus, a collimator plate 24 shown in FIG. 8(B) is fitted in the grooves 28a. These blocks 28 are made of machinable ceramics, metal, glass or the like and attached to the substrates 15 using adhesives, screws or the like. These blocks 28 are attached to the substrates 15 at other portions than the center portions of the substrates 15 and than those end portions of the substrates 15 which will be attached to the case body at a subsequent step.

According to the arrangement of the embodiment in FIG. 10, no groove is formed directly in each substrate 15, but a groove is formed in each of the blocks 28 attached to each substrate 15. This increases the degree of freedom in designing as to the material to be selected of the blocks 28, the height of each groove from the substrate and the like, causing each block 28 to be made in an optimum shape. Generally, machinable ceramics or metal can be increased in machining precision as compared with a printed circuit board for forming an electric circuit. This enables the width or the like of each groove to be precisely machined. Further, the position of each groove is higher than the surface of the substrate 15. This does not necessarily require a collimator plate having special projecting fitting portions, but a usual collimator plate may also be used with its end portions serving as fitting portions.

According to the concept of the present invention, collimator plates are fitted in the grooves such that the detector blocks, the collimator plates of the collimator device and the scintillator elements of the detector blocks are properly positioned with respect to one another. This concept can also be applied to a method of assembling an x-ray CT solid-state detector. The following description will discuss an example of this method.

Figure 11:
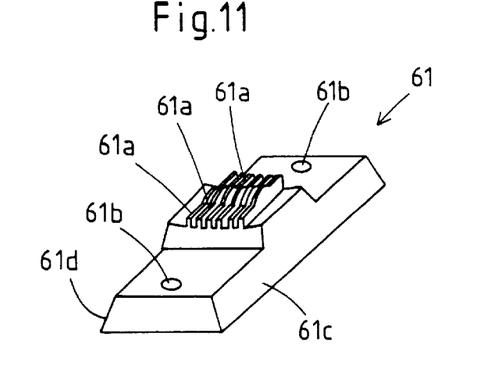
FIG. 11 is a perspective view of a jig 61 to be used in a method of assembling a solid-state detector to which the present invention is applied.
Figure 12:
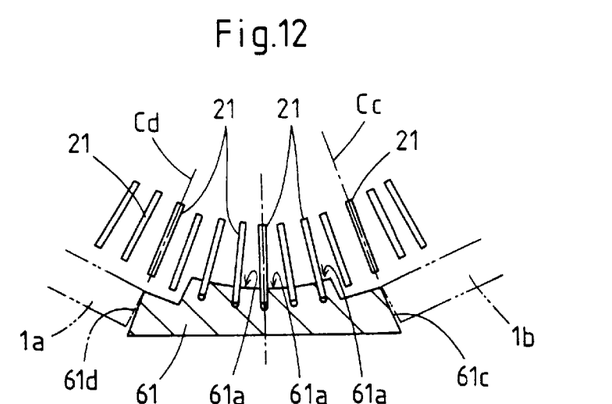
FIG. 12 is a section view, taken along a plane in the thickness direction of collimator plates 21, of the jig 61 fixed to the collimator device 2.
Figure 13:
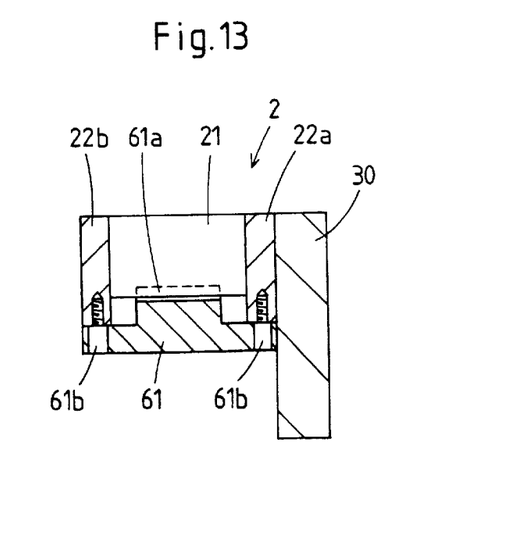
FIG. 13 is a section view, taken along a plane extending along the surface of a collimator plate 21, of the jig 61 fixed) to the collimator device 2.

FIG. 11 is a perspective view of a jig 61 used for the assembling method above-mentioned. FIG. 12 is a section view, taken along a plane in the thickness direction of collimator plates 21, of the jig 61 fixed to the collimator device 2. FIG. 13 is a section view, taken along a plane extending along the surface of a collimator plate 21, of the jig 61 fixed to the collimator device 2. In this example, the collimator device 2 has an arrangement equivalent to that shown in FIG. 3 and each detector block 1 has an arrangement equal to that shown in FIGS. 1 and 2, except that the groove plate 13 in FIGS. 1 and 2 is not included.

The jig 61 is provided in one surface thereof with a plurality of grooves 61a in each of which a collimator plate is to be fitted. At both sides of the grooves 61a, the jig 61 has through-holes 61b with the use of which the jig 61 is fixed to the supports 22a, 22b of the collimator device 2. The arrangement pitches and angles of the grooves 61a are equal to those of the collimator plates 21 of the collimator device 2. When the jig 61 is fixed to the collimator device 2, one collimator plate 21 is being fitted into each of the grooves 61a. Both end surfaces 61c, 61d of the jig 61 are so inclined as to respectively extend along the center lines Cc, Cd of the collimator plates 21 located at both ends of the jig 61. As will be discussed later, these surfaces 61c, 61d serve as reference contact surfaces based on which each detector block 1 is fixed to the collimator device 2. The distance between the upper ends of the surfaces 61c, 61d of the jig 61 is equal to the width of each detector block 1 (the distance in the direction in which the elements of each of the scintillator array 11 and the photodiode array 12 are disposed).

According to an assembling method using the jig 61 having the arrangement above-mentioned, three detector blocks can consecutively be positioned and fixed as set forth below.

Figure 14:
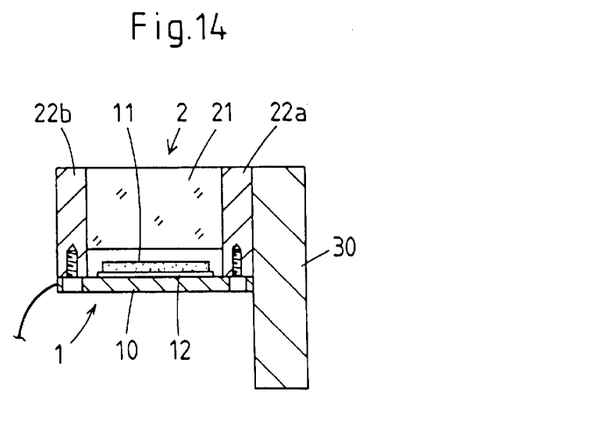
FIG. 14 is a vertical section view illustrating how a detector block 1 positioned by the method shown in FIG. 13, is fixed to the collimator device 2.

With a collimator plate 21 fitted in each of the grooves 61a as shown in FIG. 12, the jig 61 is to be fixed to the supports 22a, 22b of the collimator device 2 with bolts (not shown) through the through-holes 61b as shown in FIG. 13. More specifically, based on the designed reference contact surfaces, jigs (not shown) are disposed such that lateral sides of detector blocks 1a, 1b will come in contact with the designed reference contact surfaces, and collimator plates 21 are then fixed to these jigs (not shown). Then, these jigs (not shown) are removed. Then, the jig 61 shown by a solid line in FIG. 12 is mounted, and collimator plates 21 are fixed to this jig 61. With this jig 61 mounted, the detector blocks 1a, 1b are disposed at both sides of this jig 61 and fixed to the collimator plates from which the jigs (not shown) have been removed. Then, the detector blocks 1a, 1b are secured to the supports 22a, 22b of the collimator device 2 using bolts (not shown) as shown in the section view in FIG. 14. Then, the jig 61 is removed and the detector block 1 is disposed based on the detector blocks 1a, 1b. Thus, when the detector blocks 1a, 1b are positioned and fixed at both sides of the jig 61 and the jig 61 is then removed, the space from which the jig 61 has been removed is held by and between these two detector blocks 1a, 1b at both sides of the space. Accordingly, another detector block 1 can be positioned and fixed with the both lateral sides thereof coming in contact with lateral sides of the detector blocks 1a, 1b. Thus, three detector blocks 1a, 1b, 1 are consecutively positioned and fixed to the collimator device 2. By repeating such an operation, a number of detector blocks can consecutively positioned and fixed to the collimator device 2.

According to the assembling method above-mentioned, each detector block 1 can be simplified in arrangement. Further, each detector block 1 can properly be positioned with respect to the collimator device 2 based on the collimator plates 21. This remarkably improves the positioning precision of the scintillator elements with respect to the collimator plates as compared with the arrangement of prior art shown in FIGS. 16(A) and 16(B).

We claim:

1. An improved x-ray CT solid-state detector provided with detector blocks each having a substrate, a photodiode array secured to the substrate and a scintillator array secured to the photodiode array, and with a collimator device having a plurality of collimator plates secured to a support body, and which is arranged such that transmitted x-rays obtained by irradiating a fan-shape x-ray beam from an x-ray source onto a subject to be tested are guided to the detector blocks through the collimator device, the improvement comprising:

a single groove plate secured to each substrate having, at a predetermined position, a single groove into which a collimator plate is fitted, wherein the scintillator and photodiode arrays are secured to each substrate so as to maintain a predetermined positional relationship between said scintillator and photodiode arrays and said groove plate; and wherein each detector block and said collimator device are fixed to each other with a collimator plate fitted in said groove of said groove plate.

2. The improved x-ray CT solid-state detector according to claim 1, wherein each of said groove plates is a rectangular plate having a width equal to that of each of said substrates and is provided on a surface thereof facing said photodiode array with a projecting portion extending in the widthwise direction thereof, said groove plate being fixed to a surface of each of said substrates facing away from the scintillator array and the photodiode array secured to said substrate, wherein said projecting portion is provided at the center thereof with a convex portion, and wherein a groove is formed in the top of said convex portion, extends along the center line which divides the width of said groove plate into two equal parts, and has both a width and depth such that a collimator plate is fitted therein.

3. The improved x-ray CT solid-state detector according to claim 1, wherein the groove plate is substantially in the form of an L in section and is fixed to that surface of each of said substrates on which one of the scintillator arrays and one of the photodiode arrays are mounted, said groove plate being disposed adjacent to said arrays.

4. The improved x-ray CT solid-state detector according to claim 1, wherein the groove plate is rod-shaped and is fixed to that surface of each of said substrates on which one of the scintillator arrays and one of the photodiode arrays are mounted, said groove plate being disposed adjacent to said arrays.

5. An improved x-ray CT solid-state detector provided with detector blocks each having a substrate, a photodiode array secured to the substrate and a scintillator array secured to the photodiode array, and with a collimator device having a plurality of collimator plates secured to a support body, and which is arranged such that transmitted x-rays obtained by irradiating a fan-shape x-ray beam from an x-ray source onto a subject to be tested are guided to the detector blocks through the collimator device, the improvement comprising:

a groove provided in each substrate in a predetermined position into which a collimator plate is fitted, said groove running along a surface of said substrate facing said photodiode array, wherein scintillator and photodiode arrays are secured to each substrate with the center axes thereof aligned with the center axis of said groove, wherein one of the collimator plates to be fitted into said groove has such a shape as to stride over said scintillator array and said photodiode array, and wherein said collimator plate is fitted into said groove.

6. An improved xray CT solid-state detector provided with detector blocks each having a substrate, a photodiode array secured to the substrate and a scintillator array secured to the photodiode array, and with a collimator device having a plurality of collimator plates secured to a support body, and which is arranged such that transmitted x-rays obtained by irradiating a fan-shape x-ray beam from an x-ray source onto a subject to be tested are guided to the detector blocks through the collimator device, the improvement comprising:

a pair of blocks, each having a groove into which said collimator plate is to be fitted, are secured to each substrate at predetermined positions, the groove in each block being arranged parallel to the surface of the substrate containing said pair of blocks.

* * * * *